United States Patent

Janata

[11] Patent Number: 6,128,561
[45] Date of Patent: Oct. 3, 2000

[54] SELF-DIAGNOSTIC SYSTEM FOR CONDITIONED MAINTENANCE OF MACHINES OPERATING UNDER INTERMITTENT LOAD

[75] Inventor: Jiri Janata, Atlanta, Ga.

[73] Assignee: Georgia Tech Research Corporation, Atlanta, Ga.

[21] Appl. No.: 09/192,707

[22] Filed: Nov. 16, 1998

[51] Int. Cl.[7] .......................... G01D 21/00; F01M 11/12
[52] U.S. Cl. .......................... 701/29; 701/30; 340/438; 340/439; 340/450.3; 340/457.4; 73/117.3
[58] Field of Search ...................... 701/29, 30, 35; 340/438, 439, 449, 450.3, 457.4; 73/53.05, 117.3; 324/663, 667

[56] References Cited

U.S. PATENT DOCUMENTS

| | | | |
|---|---|---|---|
| 4,506,337 | 3/1985 | Yasuhara | 701/30 |
| 4,706,193 | 11/1987 | Imajo et al. | 701/30 |
| 5,382,942 | 1/1995 | Raffa et al. | 701/30 |
| 5,750,887 | 5/1998 | Schricker | 73/117.3 |
| 5,824,889 | 10/1998 | Park et al. | 701/29 |
| 5,969,601 | 10/1999 | Sato et al. | 701/30 |

*Primary Examiner*—Gary Chin
*Attorney, Agent, or Firm*—Thorpe, North & Western, LLP

[57] ABSTRACT

A system and method for determining the condition of lubricating oil in the oil reservoir of an oil-utilizing mechanism, said system comprising: sensor means for sensing the chemical composition of oil vapor in the head space of the oil reservoir; temperature probes for sensing the temperature of the oil and of the sensor means; microprocessor means connected to the sensor means and temperature probes for creating a vapor signature by means of a pattern recognition algorithm representing the chemical composition of the vapor in the head space; and display means for producing a discernable indication to an operator if the processor means determines that the vapor signature deviates from predetermined baseline parameters. The system is initiated when the oil-utilizing mechanism is shut off, and senses conditions periodically during the cool-down phase of the machine.

27 Claims, 4 Drawing Sheets

SELF-DIAGNOSTIC SYSTEM FOR CONDITIONED MAINTENANCE OF MACHINES OPERATING UNDER INTERMITTENT LOAD

BACKGROUND OF THE INVENTION

1. Field of the Invention

The present invention relates to a self-diagnostic system for determining maintenance conditions of lubricants in oil-utilizing machines operating under intermittent loads. More particularly, the present invention relates to a system and method for determining the condition of oil in an internal combustion engine, transmission, or the like, in order to optimize oil maintenance intervals.

2. State of the Art

Lubricating oils are typically comprised of high molecular-weight products of the petroleum distillation process. The base constituents of these oils are typically hydrocarbon chains having anywhere from 16 to 30 carbon atoms, and a boiling point higher than 350° C. Undesired constituents such as tars, asphalts, greases, and paraffin waxes are preferably removed during the refining process, and certain additives such as thickening agents, detergents, and antioxidants may be added to impart desired properties to the oil.

As oil is used in the high temperature, high stress environment of an internal combustion engine or other oil-utilizing machine, the base hydrocarbons tend to break down over time. Typically, the relatively long hydrocarbon chains of the base oil break up and degrade into oxidized forms of hydrocarbons such as polyacohols, aldehydes, carboxylic acids, esters, etc., which have inadequate or undesirable properties. When some significant proportion of the base oil has broken down in this way, the oil will no longer protect the machine from damage as desired.

At present, oil changes in internal combustion engines and similar oil-utilizing machines are typically performed according to the mileage or hours of operation of the machine, not according to the directly identified needs given by the chemical state of the lubricating oil. However, it will be appreciated that the miles driven or hours of use do not necessarily indicate the condition of the oil. For example, operation under heavy or rapidly varying loads, or under dusty or hot conditions will tend to cause oil to break down sooner than otherwise. A mileage or time-based schedule is thus only an approximation of the actual needs, based on numerous assumptions. The result is that the lubricating oil may be changed too infrequently, resulting in accumulated damage to the mechanical parts, or it may be changed more often than needed, causing needless maintenance expense and producing excessive waste oil. While one could periodically remove a sample of oil from a vehicle's oil reservoir and have it chemically tested, this is so time consuming, expensive, and inconvenient as to be essentially impractical.

It would be desirable to have a self-diagnostic system that could sense the actual chemical condition of the lubricating oil in intermittently operated machines, and provide an operator or maintenance person with an indication when the oil has reached a certain point of chemical degradation.

OBJECTS AND SUMMARY OF THE INVENTION

It is therefore an object of the present invention to provide a system for detecting the chemical condition of lubricating oil within the oil reservoir of an intermittently operating machine, such as an internal combustion engine, in order to determine the maintenance needs of the lubricant.

It is another object of the invention to provide an informational display indication that will notify a user when the lubricating oil is degraded beyond a specified point, to thus allow prompt replacement of the oil.

It is another object of the invention to provide a system for detecting the condition of lubricating oil within the oil reservoir of an internal combustion engine by a sampling/analysis sequence which is initiated when the engine is switched off and which sequence continues during engine cool-down.

It is yet another object of the invention to provide a system for sensing the composition of vapors in the head space of an oil reservoir where most sensor data acquisition occurs during the period when the engine is not in operation.

The above and other objects are realized in a system and method for determining the condition of oil in an oil-utilization mechanism which has an oil reservoir having a head space above the oil, said system comprising: a sensor means for sensing the composition of vapor in the head space and for developing a signal representing said composition; a processor for receiving the signal and for determining if the signal corresponds to predetermined parameters; and apparatus for producing a discernable indication if the processor determines that the signal deviates from the predetermined parameters.

In accordance with one aspect of the invention, a system for sensing the composition of vapors within an oil reservoir of an internal combustion engine initiates a sampling/analysis sequence when the engine is switched off, which sequence continues during engine cool-down.

Other objects and features of the present invention will be apparent to those skilled in the art, based on the following description, taken in combination with the accompanying drawings.

DETAILED DESCRIPTION OF THE PREFERRED EMBODIMENT

Figure 1:
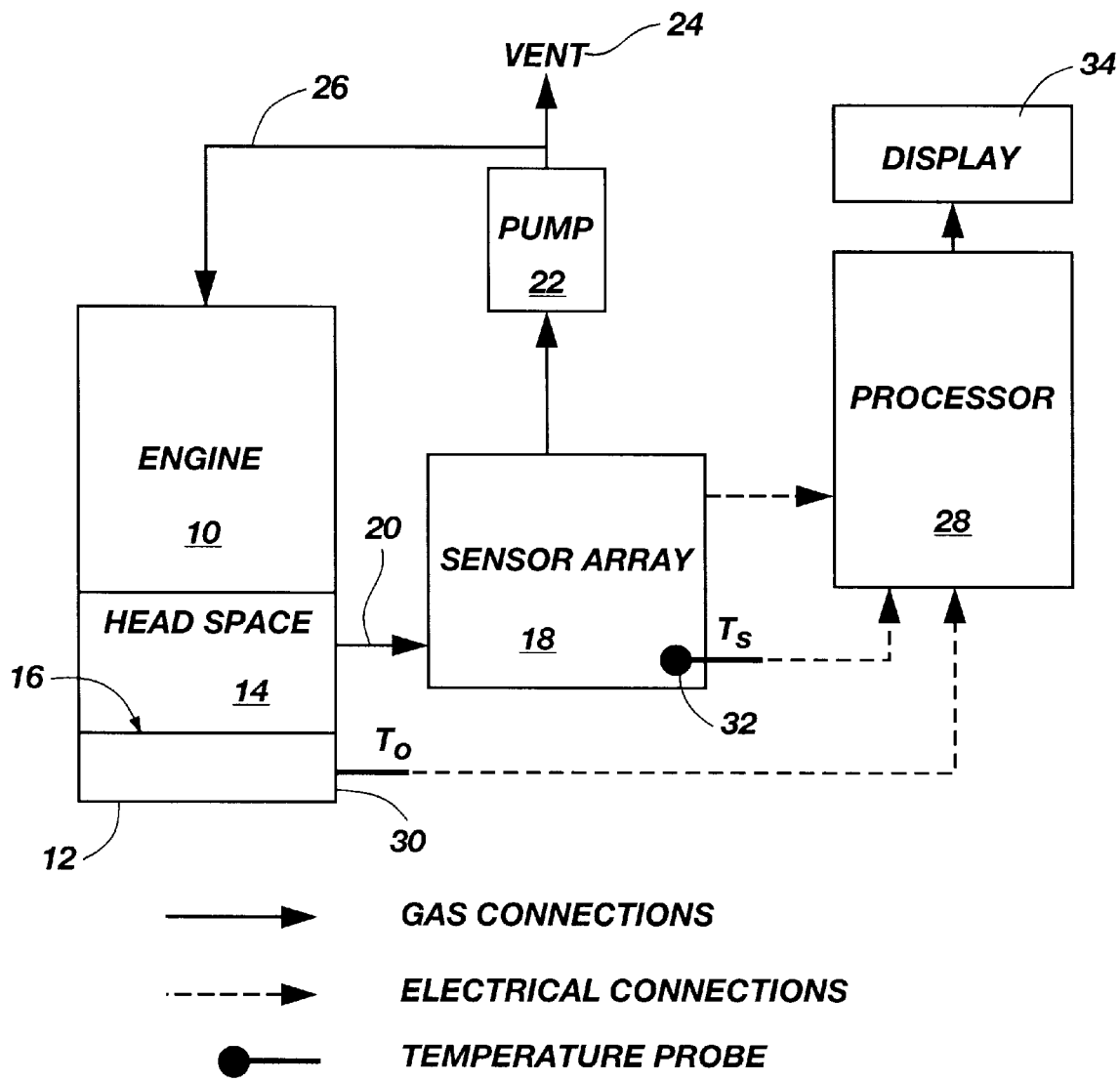
FIG. 1 is a schematic diagram of one embodiment of the self-diagnostic system of the present invention installed in an internal combustion engine.

FIG. 1 is a schematic diagram of one embodiment of the self-diagnostic system of the present invention. Shown is an engine 10 with an oil reservoir 12, such as the crankcase of the engine, having a head-space 14 above the free surface 16 of the oil. Alternatively, it will be apparent that instead of an engine, the present invention could be used in a transmission of an internal combustion engine, or other similar oil-utilizing machine subject to intermittent use and having an oil reservoir.

A sensor array 18 is disposed in communication with the head space 14 via a conduit 20 which will allow the head-space vapors to travel to the array for sampling. The vapors are transported through the conduit 20 by means of a micropump 22 which creates suction to draw the vapors to and through the sensor array. The vapors are then exhausted to the outside through a vent 24 after sensing. Alternatively, if required for environmental or other reasons, the vapors may be circulated back into the engine, for example for combustion, through another conduit 26.

The mixture of volatile degradation products in the head-space above the lubricant represents a chemical signature that identifies the composition, i.e., the state of the oil. As noted above, these degradation products of the oil are typically oxidized forms of hydrocarbons including C6–C20 aliphatic carboxylic acids, C6–C14 carboxylic aldehydes, C6–C14 aliphatic esters, and C6–C12 unsaturated aldehydes. Chemical changes taking place in the lubricating oil may be detected by sensing the changes of composition of these volatile degradation products in the gas phase (head-space) above the lubricant. As will be apparent to one knowledgeable in the field, the presence of these degradation products increases as the oil becomes progressively more degraded over time. These volatile combustion products are in a dynamic equilibrium with the components of the oil and indicate the status of the lubricant, i.e. the need for replacement.

The sensing array 18 preferably consists of 6 to 10 sensing elements, each preferably sensitive to a different degradation component of the oil. A greater number of sensing elements (i.e. more than 10) could be provided if desired for more complete and accurate sampling of the head-space vapors, but are not necessary for adequate implementation of the present invention. The sensing elements may be electrochemical, optical, mass, thermal, or any combination thereof to form an array. The preferred sensor type is an electrochemical sensor which detects conductivity changes. See J. Janata, *Principles of Chemical Sensors* (New York, Plenum Press, 1989). One example of such a sensor is a semiconducting tin oxide type sensor such as the Figaro TGS series available from Figaro Engineering, Inc., Japan.

The detected change of the head-space composition constitutes a typical chemical signature corresponding to the state of the lubricant. Fresh oil also has a characteristic signature which, in the conditioned-maintenance system of the present invention, represents the baseline against which the progressive degradation is measured.

The sensor array 18 is connected to a microprocessor 28 which receives signals from the various sensing elements. The processor 28 also receives signals from a temperature probe 30 disposed in the oil reservoir 12 to detect the temperature of the oil, and from another temperature probe 32 disposed adjacent to the sensor array 18 to detect the temperature of the sensor array. The oil reservoir temperature probe 30 is important to the system of the present invention because the rate of change of the composition head-space vapors varies as a function of the temperature of the oil. The sensor array temperature probe 32 is employed because the performance of the sensor array depends in part on its operating temperature, which may vary significantly from the temperature of the oil.

Figure 2:
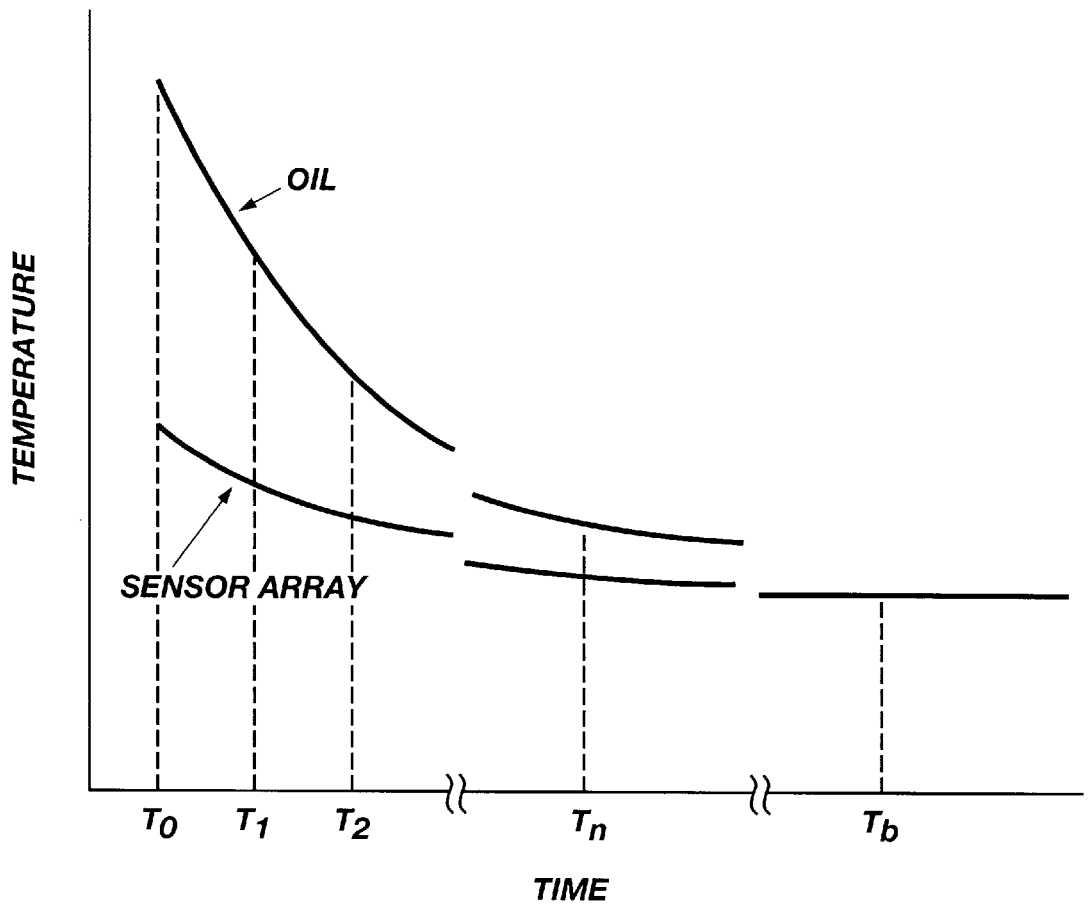
FIG. 2 is a graph of an illustrative cool-down temperature curve of engine oil and sensor array of an internal combustion engine beginning at engine shut-down.

The sensing array will absorb heat from the engine and from the head-space vapors, but may be physically separated some distance from the engine itself, and typically will not attain the same temperature as the engine oil, as shown by the curve of FIG. 2. Consequently, the cooling curve response profile must be corrected for the effects of the temperature changes of the sensing array itself, which should be independently measured. Those skilled in the art will recognize that correcting the response profile can be easily done by normalizing the cooling curve to the difference in temperature between the oil and the sensing array.

Additionally, the performance of most sensors is degraded when they must operate under vibration. This is particularly true of mass sensors. Because the invention here described acquires data when the engine is not in operation, it operates in an essentially vibration free environment. It will be apparent that this configuration will enhance both the performance and useful life of the sensors. Moreover, by operating when the engine is not in use, a generous amount of time is made available for data acquisition and data processing.

The microprocessor 28 analyzes the signals transmitted to it, and provides output in a user-friendly format such as through an indicator light, CRT, or other visual display 34, or alternatively, through other indications such as audible signals, to notify the user or maintenance personnel of the condition of the oil. It will be apparent to those skilled in the art that other modes of output may also be advantageously employed to accomplish the same purpose.

The system of the present invention uses a novel sampling/analysis sequence, which is initiated when the engine 10 is shut off or some preprogrammed delay time thereafter, and the oil begins to cool down. A graph of the cool-down temperature curve of the engine oil and sensor array beginning at engine shut-down is provided in FIG. 2. As the temperature of the oil decreases after engine shut-down, the chemical composition of the head-space vapors changes according to the type and concentration of its volatile components. The most volatile components, such as aliphatic esters and alcohols, stay in the gas phase the longest, while the least volatile components, such as aliphatic acids and aldehydes, disappear. As noted above, the rate of these composition changes is a function of the temperature of the oil.

The response from the integrated chemical sensing array 18 is obtained at pre-determined temperature intervals during the cool-down phase, shown as $T_0$, $T_1$, $T_2$, and so forth in FIG. 2, and is evaluated by the on-board microprocessor 28 to determine a signature of the oil vapors. A three-dimensional representation of the time- and temperature-dependent dynamic vapor signature of the oil reservoir vapors is given in FIG. 3. In this figure the several discrete peaks represent the time and temperature dependent signature of the various constituent degradation products present in the oil vapor. The three-dimensional graph thus represents a landscape or signature of either "good" or "bad" oil. The absolute values, positions, or number of peaks in this landscape do not have any particular meaning except as an indication of the state of the oil. The mode of analysis is similar to the decision made by an experienced wine taster who does not know the composition of the wine, but can nevertheless determine the type, quality, and even the vintage of the product. This approach is commonly known as artificial intelligence or in the case of gas sensing, "electronic nose." The strategy for recognizing the patterns of like complex mixtures is called pattern recognition.

Figure 4:
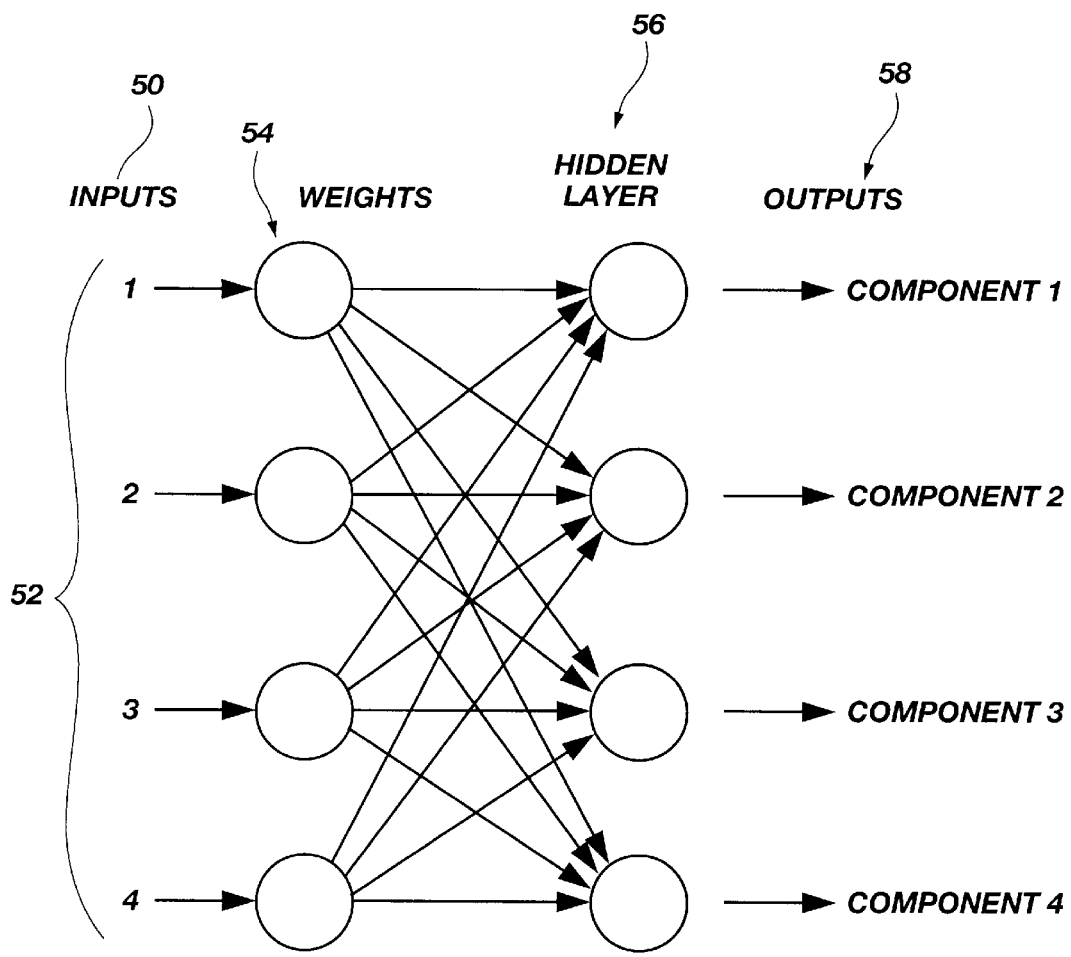
FIG. 4 is a schematic diagram of an artificial neural network for accepting inputs from a plurality of sensors in order to create a dynamic vapor signature.

There are several pattern recognition packages available to perform this task. One such technique is called Artificial Neural Networks or ANN. See D. E. Rumelhart, G. E. Hinton, R. J. Williams, "Learning Representations by Back Propagating Erros", 323 *Nature* 533–536 (1986). A scheme for ANN as part of the present invention is shown in FIG. 4. Raw inputs 50 from an array 52 consisting of a plurality of sensors (four sensors shown for simplicity) are fed into the first input layer of amplifiers 54. From there, the outputs are fed to a plurality of elements of hidden layer amplifiers 56 which multiply the inputs by a predetermined coefficient during the "learning" phase of the ANN. The "learning" is performed automatically by presenting the ANN with the mixture of known composition and adjusting the outputs from the output layer 56 to the desired values. The time- and temperature-dependent dynamic vapor signature of the oil vapors is determined by the configuration of the entire group of output values 58 at a plurality of sampling times during the sampling cycle.

This "learning" of the ANN is performed for the "good" oil and the values of the amplification factors are permanently stored, such as in computer memory, as the signature of the "good" oil. The ANNs can be implemented either in the software or in the hardware form. As noted, the absolute concentrations of individual degradation products in the head space or their algorithmic relationship to the composition of the oil is not necessary.

Another pattern recognition algorithm that may be advantageously employed in the present invention is called Visual Empirical Region of Influence (VERI), developed at Sandia National Laboratories. See G. C. Osbourn, J. W. Bartholomew, A. J. Ricco, and G. C. Frye, "Visual-Empirical Region-of-Influence Pattern Recognition Applied to Chemical Microsensor Array Selection and Chemical Analysis", 31 *Account of Chemical Research* 297–307 (1998). VERI computes distances between data points in the n-dimensional space (where n is the number of sensors in the sensing array). The training or "learning" of this algorithm is similar to ANN, again based on the response of the array to the known standard. In both ANN and VERI pattern recognition techniques the deviation of the actual signature (i.e. progressively deteriorating oil) is compared with the baseline or standard signature (i.e. the "good" oil). The microprocessor "decision" whether to advise changing the oil or not is based on the chosen magnitude of acceptable deviation between "good" oil and "bad" oil.

Figure 3:
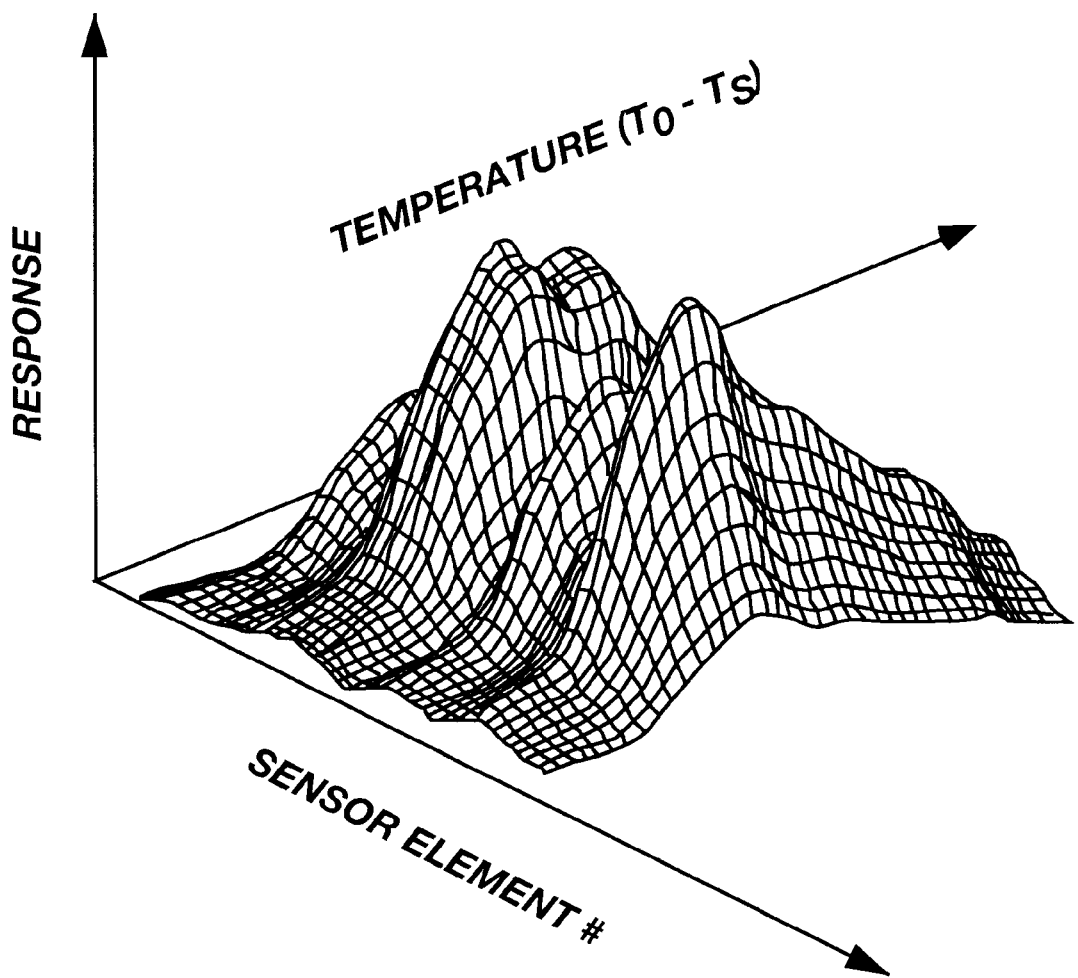
FIG. 3 is a representation of the three-dimensional time- and temperature-dependent dynamic vapor signature of the oil reservoir vapors.

The preferred diagnostic schedule would be as follows. The engine is operated for a minimum predetermined time and reaches a standard operating temperature. The corresponding temperature of the oil is $T_0$ (FIG. 2). The diagnostic sequence commences immediately after the engine ceases its operation. The response of the head-space changes is recorded at different points, $T_0$, $T_1$, $T_2$, etc., on the cooling curve (FIG. 2). This time-and- temperature-dependent "dynamic" information for each sensor becomes a part of the diagnostic test (FIG. 3).

After the engine cools down completely, the baseline value of the "signature" $T_b$ is obtained. Because of its design, the diagnostic system of the present invention is self-calibrating since the composition of the head-space under a cooled-down condition is expected to be constant or nearly constant. Both the "cold" and the "hot" signatures are compared to the "cold" and the "hot" signatures corresponding to the fresh oil, and the deviation of these signatures provides the desired information about the required lubricant change.

This information is made available in a user-friendly form prior to initiating the next duty cycle. The typical scenario for a motor vehicle, according to this scheme, can be described as follows: The vehicle is operated for a minimum required time and then parked. The diagnostic sequence starts immediately (or, alternatively, after a selected delay). The data is obtained and analyzed during the rest period, and after complete cool down the system calibrates itself. The microprocessor retains in memory the calibration signature, and the cycle is repeated again. The microprocessor compares the calibration signatures of the n'th and the n-1 run, and the results are made available to the operator prior to the next duty cycle with appropriate recommendations for action.

Monitoring of the chemical status of the oil is the great advantage of the present invention, and is the fundamental idea behind condition-based maintenance. Instead of following a necessarily approximate mileage or hours of operation schedule for oil changes, maintenance can be scheduled based on the directly identified needs given by the chemical state of the lubricant. Condition-based maintenance thus saves both labor and material costs in engine maintenance, as well as decreases the volume of pollutants such as waste oil discarded into the environment. The main distinguishing feature of the present invention is that the information acquisition is done dynamically by a multi-sensing array while the engine is not operating.

Another significant advantage of the present invention is the baseline time determination feature. The data collection of this invention relies on the time dependent changes of the head space composition (profile) collected after each duty cycle. Turning the engine off provides a precise determination of t=0 from which the data acquisition during the cooling period begins. Thus, the time dependence of the profiles of the composition of the head space becomes the part of the signature of the "good" or "degraded" lubricant. The "zero time" aspect of this information acquisition prevents one notorious problem of chemical sensors/arrays: baseline drift. That is, each $T_n=0$ for the n-th profile establishes a new baseline. That type of information and such benefits would not be available for monitoring of the head space above the lubricants in continuously operating systems, e.g. in transformer oil because the profile at t=0 could not be accurately established.

This self-diagnostic system could be implemented in a wide variety of applications. For example, it would be ideal for the military for engines that are operated under widely varying conditions and loads where time dependent maintenance schedules are difficult to estimate. It could also be used in the civilian sector such as for construction and heavy earth moving machinery, in private automobiles, commercial and private aircraft, ships, and so forth where maintenance schedules are more easily predicted, but may still be unrealistic. In all cases, the use of such a system would result in decreased maintenance labor and material costs, decreased environmental waste, and increased useful lifetime of the machines.

It is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements.

What is claimed is:

1. A system for determining the condition of oil in an oil-utilizing machine which has an oil reservoir from which oil is pumped to circulate to various parts of the machine for lubrication thereof, and to which oil is returned when not being circulated, said reservoir being larger than the volume of oil normally utilized to define a head space above the oil in the reservoir, said system-comprising:

sensor means for sensing the composition of vapor in said head space in said reservoir and for developing a signal representing said composition;

processor means for receiving said signal and for comparing it to predetermined baseline parameters; and means for producing a discernable indication when the processor means determines that the signal deviates from said predetermined baseline parameters.

2. The system as described in claim 1, further comprising:

a first temperature probe disposed in said oil reservoir for sensing the temperature of the oil, and for developing a signal representing said oil temperature; and a second temperature probe for sensing the temperature of the sensor means and for developing a signal representing said sensor means temperature; and processor means including means for receiving the signals from the first and second temperature probes to develop a time and temperature based vapor signature representing the condition of the oil, and for comparing said signature to the predetermined baseline parameters in conjunction with the signal from the sensor means to determine whether the sensor means signal deviates from said predetermined baseline parameters.

3. The system as described in claim 2 wherein said processor means includes means for receiving a series of signals from said sensor means and from said first and second temperature probes at certain times corresponding to predetermined temperatures of the oil as it cools down following shut off of the machine, the first signals being received when the oil-utilizing machine is shut off, and the last signals being received when the oil temperature has reached approximate thermal equilibrium with the external environment, said last signals representing a baseline time and temperature based vapor signature representing the condition of the oil.

4. The system as described in claim 3 wherein said processor means includes means for determining whether the series of signal corresponds to the predetermined baseline parameters according to a pattern recognition algorithm.

5. The system as described in claim 4 wherein said sensor means comprises a plurality of sensors, each for directly detecting the concentration of one of a plurality of gaseous-phase lubricating oil degradation products in the head space.

6. The system as described in claim 4 wherein said sensor means comprises a plurality of sensors, each configured for directly detecting within the head space the concentration of a gaseous-phase lubricating oil degradation product selected from the group consisting of C6–C20 aliphatic carboxylic acids, C6–C14 carboxylic aldehydes, C6–C14 aliphatic esters, and C6–C12 unsaturated aldehydes.

7. The system as described in claim 1 wherein said means for producing a discernable indication is selected from the group consisting of an indicator light, a CRT display, an LCD display, a gauge, and an audible signal.

8. The system as described in claim 1 wherein said oil-utilizing machine is chosen from the group consisting of an internal combustion engine and a mechanical transmission.

9. A system for determining the condition of lubricating oil in the oil reservoir of an internal combustion engine, said reservoir being larger than the volume of oil normally utilized to define a head space above the oil in the reservoir, said system comprising:

sensor means having a plurality of sensors, each sensor for directly detecting the concentration of one of a plurality of gaseous-phase lubricating oil degradation products in the head space, and for developing a signal representing said concentrations;

pumping means for pumping vapor from the head space of said oil reservoir to the sensor means;

a first temperature probe disposed in said oil reservoir for sensing the temperature of the oil and for developing a signal representing said oil temperature;

a second temperature probe disposed in said sensor means for sensing the temperature of the sensor means and for developing a signal representing said sensor means temperature;

processor means connected to said sensor means and to said first temperature probe and said second temperature probe for receiving said signals and for determining whether the signals correspond to predetermined baseline parameters; and display means for producing a discernable indication to an operator when the processor means determines that the signals deviates from said predetermined baseline parameters.

10. The invention as described in claim 9 wherein each of said plurality of sensors are configured for directly detecting the concentration of a gaseous-phase lubricating oil degradation product selected from the group consisting of C6–C20 aliphatic carboxylic acids, C6–C14 carboxylic aldehydes, C6–C14 aliphatic esters, and C6–C12 unsaturated aldehydes.

11. The invention as described in claim 9 wherein said display means for producing said discernable indication is selected from the group consisting of an indicator light, a CRT, an LCD display, a gauge, and an audible signal.

12. The invention as described in claim 9 wherein said processor means includes means for receiving a series of signals from said sensor means and from said first and second temperature probes at certain times corresponding to predetermined temperatures of the oil as it cools down following shut off of the machine, the first signals being received when the oil-utilizing machine is shut off, and the last signals being received when the oil temperature has reached approximate thermal equilibrium with the external environment.

13. A method for monitoring the condition of lubricating oil in an oil-utilizing machine having an oil reservoir from which oil is pumped to circulate to various parts of the mechanism for lubrication thereof and to which oil is returned when not being circulated, said reservoir being larger than the volume of oil normally utilized to define a head space above the oil in the reservoir, said method comprising the steps of:

(a) operating said machine until the lubricating oil reaches at least a standard operating temperature;

(b) shutting off the machine;

(c) pumping a sample of vapor from the head space of said oil reservoir to a sensor means;

(d) sensing the composition of the vapor with the sensor means and developing a signal representing said composition;

(e) sensing the temperature of the oil in the oil reservoir and developing a signal representing said oil temperature;

(f) sensing the temperature of the sensor means and developing a signal representing said sensor means temperature;

(g) processing the signals representing the composition of the vapor, the temperature of the oil, and the temperature of the sensor means, with a processor means for comparison of said signals to predetermined baseline parameters;

(h) repeating steps c through g periodically over a time interval approximately equal to the time required for the oil to cool down to an equilibrium temperature with the exterior environment of the oil-utilizing machine, thereby allowing the processor means to calculate a time and temperature based vapor signature representing the condition of the oil for comparison with a predetermined baseline time and temperature based vapor signature, the above steps a through h representing a single operating cycle of the machine; and (i) producing a discernable indication to an operator when the processor means determines that the time and temperature based vapor signature deviates from said predetermined baseline time and temperature based vapor signature.

14. The method as described in claim 13 wherein the processor means calculates the time and temperature based vapor signature representing the condition of the good oil using a pattern recognition algorithm.

15. The method as described in claim 14 wherein said predetermined baseline time and temperature based vapor signature is determined by the steps of:

(j) filling said oil reservoir with good oil;

(k) performing steps a through h to complete one operating cycle of the machine and to create a time and temperature based vapor signature of the good oil; and (l) retaining the time and temperature based vapor signature of the new oil in memory in the processor means as the predetermined baseline time and temperature based vapor signature.

16. The method as described in claim 13 wherein said oil-utilizing machine is chosen from the group consisting of an internal combustion engine and a mechanical transmission.

17. The method described in claim 13 wherein said discernable indication is selected from the group consisting of an indicator light, a CRT, an LCD display, a gauge, and an audible signal.

18. The method described in claim 13 wherein the sensor means senses the composition of the vapor by detecting the concentration of gaseous-phase degradation products of oil selected from the group consisting of C6–C20 aliphatic carboxylic acids, C6–C14 carboxylic aldehydes, C6–C14 aliphatic esters, and C6–C12 unsaturated aldehydes.

19. A system for determining the condition of oil in an oil-utilizing machine which has an oil reservoir from which oil is pumped to circulate to various parts of the machine for lubrication thereof, and to which oil is returned when not being circulated, said reservoir being larger than the volume of oil normally utilized to define a head space above the oil in the reservoir, said system comprising:

a sensor configured for sensing the composition of vapor in said head space in said reservoir and for developing a signal representing said composition; and a processor configured for receiving said signal and for comparing it to predetermined baseline parameters to determine the condition of the oil.

20. The system as described in claim 19, further comprising:

a first temperature probe disposed in said oil reservoir for sensing the temperature of the oil, and for developing a signal representing said oil temperature; and a second temperature probe for sensing the temperature of the sensor and for developing a signal representing said sensor temperature; and wherein the processor is configured for receiving the signals from the first and second temperature probes to develop a time and temperature based vapor signature representing the condition of the oil, and for comparing said signature to the predetermined baseline parameters in conjunction with the signal from the sensor to determine whether the sensor signal deviates from said predetermined baseline parameters.

21. The system as described in claim 20 wherein said processor is configured for receiving a series of signals from said sensor means and from said first and second temperature probes at certain times corresponding to predetermined temperatures of the oil as it cools down following shut off of the machine, the first signals being received when the oil-utilizing machine is shut off, and the last signals being received when the oil temperature has reached approximate thermal equilibrium with the external environment, said last signals representing a baseline time and temperature based vapor signature representing the condition of the oil.

22. The system as described in claim 21 wherein said processor is configured for determining whether the series of signals corresponds to the predetermined baseline parameters according to a pattern recognition algorithm.

23. The system as described in claim 22 wherein said sensor comprises a plurality of sensors, each for directly detecting the concentration of one of a plurality of gaseous-phase lubricating oil degradation products in the head space.

24. The system as described in claim 22 wherein said sensor comprises a plurality of sensors, each configured for directly detecting within the head space the concentration of a gaseous-phase lubricating oil degradation product selected from the group consisting of C6–C20 aliphatic carboxylic acids, C6–C14 carboxylic aldehydes, C6–C14 aliphatic esters, and C6–C12 unsaturated aldehydes.

25. The system as described in claim 19, further comprising an indicator configured for producing a discernable indication when the processor determines that the signal deviates from said predetermined baseline parameters.

26. The system as described in claim 25 wherein said indicator is selected from the group comprising an indicator light, a CRT display, an LCD display, a gauge, and an audible signal.

27. The system as described in claim 19 wherein said oil-utilizing machine is chosen from a group consisting of an internal combustion engine and a mechanical transmission.

* * * * *